United States Patent [19]

Eckbreth et al.

[11] 4,176,960
[45] Dec. 4, 1979

[54] SPATIAL RESOLUTION ENHANCEMENT IN COAXIAL LIGHT SCATTERING SYSTEMS

[75] Inventors: Alan C. Eckbreth, Glastonbury; Jack W. Davis, East Hartford, both of Conn.

[73] Assignee: United Technologies Corporation, Hartford, Conn.

[21] Appl. No.: 858,937

[22] Filed: Dec. 9, 1977

Related U.S. Application Data

[63] Continuation-in-part of Ser. No. 624,491, Oct. 21, 1975, abandoned.

[51] Int. Cl.² ............................................. G01N 21/22
[52] U.S. Cl. ..................................... 356/338; 250/574
[58] Field of Search ................ 356/103, 104, 75, 337, 356/338, 341, 342, 301; 250/574

[56] References Cited

U.S. PATENT DOCUMENTS

| 3,068,739 | 12/1962 | Hicks, Jr. et al. | 350/96.26 |
| 3,992,103 | 11/1976 | Tyley et al. | 356/103 X |
| 4,017,186 | 4/1977 | Shofner et al. | 250/574 X |

OTHER PUBLICATIONS

Smith, Warren J., *Modern Optical Engineering*, McGraw-Hill, New York, 1966, p. 333.

Primary Examiner—Conrad J. Clark
Assistant Examiner—Bruce Y. Arnold
Attorney, Agent, or Firm—M. P. Williams

[57] ABSTRACT

In an optical system, primarily adapted for use in light scattering diagnostics e.g. Raman, Rayleigh, laser fluorescence, an obscuration means is placed between the sample volume (or object) and a light collecting means (such as a lens or mirror) to limit the backscattered light collection passed through an aperture to a shorter length along the optical axis, thereby increasing the spatial resolution of the system. In general, the effective obscuring diameter is determined as twice the ratio of the square of the distance between the image of the aperture within the sample volume and the collection means to the distance between the collection means and the aperture, times the ratio of the aperture diameter to the desired length of sample volume. In refractive embodiments, obscuration is provided by an opaque disc adjacent a collection lens. In a second embodiment, obscuration is provided by a coaxial arrangement of independent fiber optical light pipes. In a third embodiment, Cassegrainian-type reflection optics are used.

5 Claims, 4 Drawing Figures

SPATIAL RESOLUTION ENHANCEMENT IN COAXIAL LIGHT SCATTERING SYSTEMS

CROSS REFERENCE TO RELATED APPLICATIONS

This application is a continuation-in-part of our prior application Ser. No. 624,491, filed Oct. 21, 1975, now abandoned.

BACKGROUND OF THE INVENTION

1. Field of Invention

This invention relates to optical systems, and more particularly to improved spatial resolution along the optical axis of a coaxial optical system, primarily adapted for use in light scattering diagnostics.

2. Description of the Prior Art

The phenomenon known as Raman scattering has for many years been utilized as a laboratory tool in studying the structure of molecules and the characteristics of the solid state. With the recent increase of laser technology, highly sensitive photodetector systems, and processing capabilities, Raman scattering techniques are increasingly being applied to fluid mechanics and combustion and in such diverse arts as meteorology, atmospheric pollution monitoring, exhaust gas analysis, industrial process control, and the like. In a typical apparatus which will serve as an exemplary basis for discussion herein, Raman scattering techniques may be employed using a system which irradiates an object, such as a volume of hot gases in the exhaust effluent of a jet engine, with a finely collimated beam of energy, such as provided by a laser, while viewing a portion of the axis so illuminated with an optical system at right angles to the axis of the source. The optical system typically includes a collection lens or mirror (which may be comprised of a pair of individual lenses for improved control over aberrations, or may be a Cassegrainian primary), focusing lenses, optically responsive means to convert to electric signals, and some form of processing, in dependence on the particular phenomenon which is under study. A wide variety of systems of this general type, and the underlying theories of physics relating thereto, and adequately disclosed in Lapp and Penney, "Laser Raman Gas Diagnostics", Plenum Press: New York, 1974. Therefore, further detail relating to the known art of Raman gas diagnostics is not given herein.

Substantially all Raman experiments reported to date are performed with viewing geometries having very large angles (that is, that the viewing optics are at right angles or large angles with respect to the axis of the radiation source), for several reasons. First, Raman scattering is extremely weak, requiring ten orders of magnitude or more greater irradiation power than the power of the resulting optical signal to be sensed. As the angle decreases, and particularly where coaxial arrangements are used (in which the radiating source irradiates the specimen or sample volume from the same direction as the collecting optics views the specimen), the amount of spurious backscattered light increases dramatically. The weak Raman scattering effect is frequently completely swamped and unable to be detected amidst the high amount of backscattering in a coaxial configuration. A second problem with small angle viewing geometries is that the spatial resolution obtained by coincidence of two axes degrades markedly as the viewing angle approaches the irradiation angle. When the angles are the same (in a coaxial configuration), the inherent area along the axis of irradiation which is collected by the optic system (when a refractive, two-lens system is used) is from half the focal length to infinity. Since temperature profiles and other phenomena are liable to vary significantly over a small fraction of this collection area, there is a tendency for averaging or masking of the results being sensed to the point that no significant information can be derived by coaxial Raman scattering techniques. This effect is lessened somewhat in that the fractional contribution of light collected by an optical system is concentrated near the focal point; but since the effects being sensed can vary by two or more orders of magnitude at points quite close to the focal point, the actual responses in the gases being analyzed may in fact be far greater than the collection concentration ratio, such that the effect actually being monitored may be outside of the high-percentage region of the illuminating subject.

However, there are many instances where the utilization of large-angle (or right-angle) viewing geometries are undesirable. For instance, where only a single aperture is provided in an existing system, it may be totally impossible to provide a second aperture to permit a wide angle geometry system to be utilized for diagnosing a specimen within the aperture. Additionally, the specimen may be contained within an annular chamber or the like where the geometrical association of a wide-angle viewing geometry would be impossible.

SUMMARY OF THE INVENTION

An object of the present invention is providing increased spatial resolution in an optical system; another object of the invention is providing improvements in optical systems adapted for light scattering diagonstic techniques.

According to the present invention, the axial extent of a sample volume, from which backscattered radiation is provided by collection means through an aperture to optically responsive means, is limited to a desired length by obscuration means having an effective obscuring diameter related inversely to said desired length. According further to the invention, the effective obscuring diameter is, in general, equal to twice the square of the distance between the collection means and the image of the aperture in said sample volume times the diameter of the aperture, divided by the product of said desired length and the distance between the collection means and the aperture.

The present invention provides significant improvements in the spatial resolution of an optical system having a viewing geometry coaxial with the irradiation. Specifically, the invention limits the length of the sample volume which is visible to the optically responsive means (e.g. detector), in a very precise manner. The invention provides accurate, quantitative limitation of the length of the sample volume by controlling the effective obscuring diameter of an obscuration means as a function of such desired length and of the size and spacing of the aperture.

Other objects, features and advantages of the present invention will become more apparent in the light of the following detailed description of preferred embodiments thereof, as illustrated in the accompanying drawing.

DETAILED DESCRIPTION

Figure 4:
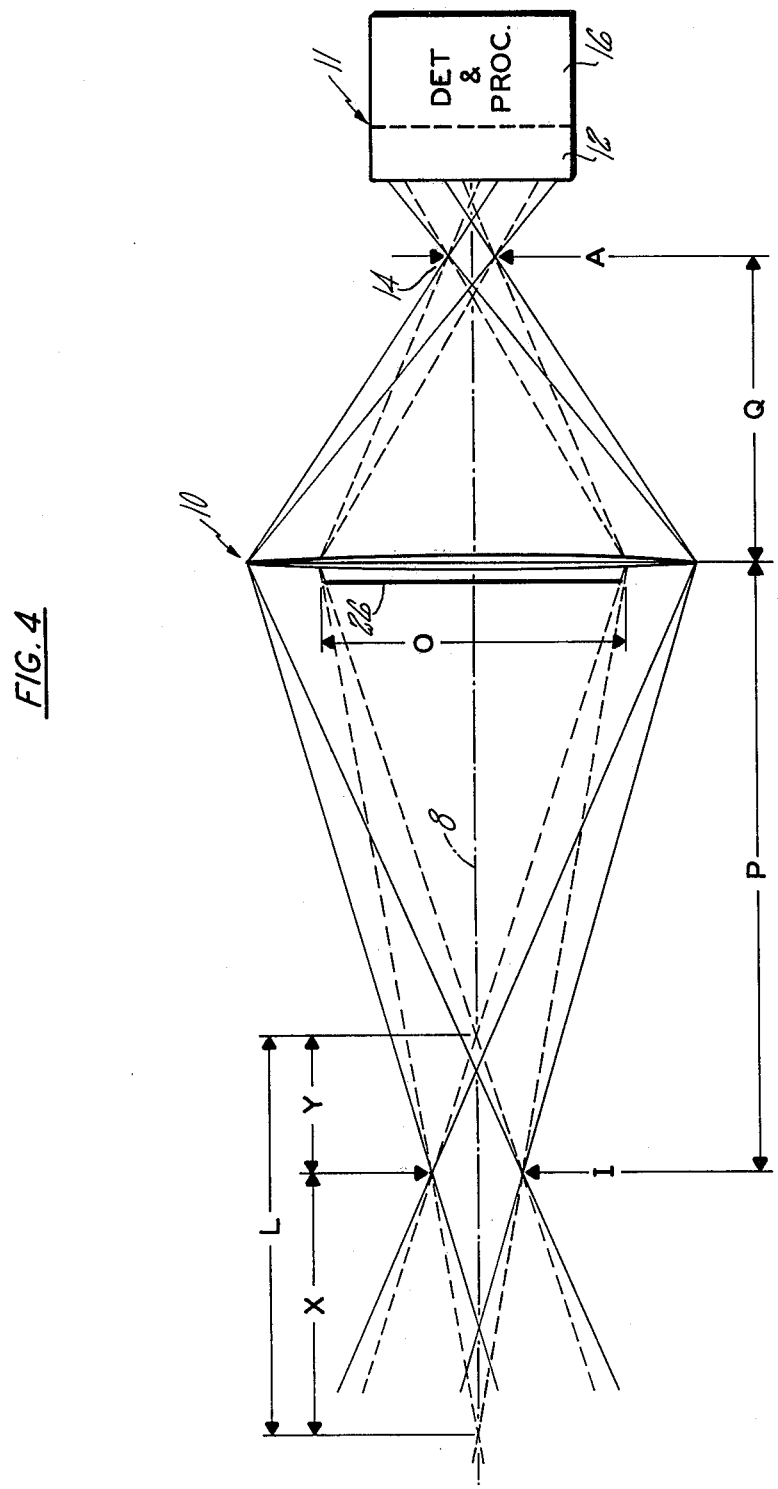
FIG. 4 is a schematic illustration of the general principles of the present invention.

Referring first to FIG. 4, a line drawing, not at all to scale, illustrates the principles of the present invention. FIG. 4 illustrates, in general, an optical system having an axis 8 along which there is coaxially disposed a collection means 10, illustrated in FIG. 4 as a thin lens. An optically responsive means 11 may include a collimating lens 12 to provide illumination, received through an aperture 14 from the collection means 10, to detecting and processing means 16. The aperture 14 has a diameter A (as illustrated to the right in FIG. 4) and is spaced a distance Q from the collection means 10 where the distances P and Q are related to the focal length f of a symmetrical thin lens by the relationship:

$$1/f = 1/P + 1/Q \quad (1)$$

and, the diameter, I, of the image of the aperture is, through simple geometry, $$I = PA/Q \quad (2)$$

The present invention provides a sample volume in a region surrounding the image of the aperture (I) which is limited in axial extent to a desired length L, which, as illustrated in FIG. 4, is defined as:

$$L = X + Y, \quad (3)$$

where X is the distance between the image of the aperture (I) and the extreme distal end of the sample volume (where the dotted lines cross), and Y is the distance between the image of the aperture (I) and the extreme proximal end of the sample volume. Reference to FIG. 4 illustrates that the length L of the sample volume is determined by the effective obscuring diameter, O, of an obscuration means 26 in combination with the aperture A. Whenever the term "effective obscuring diameter" or its shorthand equivalent "O" are used herein, what is meant is the projection of the obscuration means 26 on the collection means 10, as defined hereinafter. In FIG. 4, the obscuration means 26 may be a disc, and its effective obscuring diameter is the projection of it against the thin lens. If the obscuration means 26 is adjacent and touching the collection means 10, then its actual diameter is its effective obscuring diameter; but if the obscuration means is a disc or other surface which is positioned to the left (as seen in FIG. 4) from the collection means 10, then its effective obscuring diameter will be greater than its actual diameter by a ratio determined from the simple geometric relationships illustrated in FIG. 4.

The length L of the sample volume can be controlled, in accordance with the invention, by the relationship of the effective obscuring diameter, O, with the diameter of the aperture, A. This is derived from the simple geometry illustrated in FIG. 4, as follows:

$$X/I = (X + P)/O \quad (4)$$

$$XO = IX + IP \quad (5)$$

$$X(O - I) = IP \quad (6)$$

$$X = IP/(O - I) \quad (7)$$

and $$Y/I = (P - Y)/O \quad (8)$$

so $$Y = IP/(O + I) \quad (9)$$

$$L = X + Y = \frac{IP}{O - I} + \frac{IP}{O + I} = \frac{IP(O + I + O - I)}{O^2 - I^2} \quad (10)$$

$$L = 2IPO/(O^2 - I^2) \quad (11)$$

Substituting (2) into (11):

$$L = \frac{2P\left(\frac{PA}{Q}\right)O}{O^2 - \frac{P^2 A^2}{Q^2}} = \frac{2P^2 AO}{Q(O^2 - \frac{P^2 A^2}{Q^2})} \quad (12)$$

In practical systems, the diameter of the collection means 10, and of the obscuration means 26, would be one or two orders of magnitude greater than the diameter of the aperture A. In such a case, $$O >> A, \; O^2 >>> (P^2 A^2 / Q^2) \quad (13)$$

and $$L \sim 2P^2 A / QO \quad (14)$$

And, considering the small variation in length, L, due to the assumption of (13), the effective obscuring diameter, O, is defined herein as that which provides the desired length L, as follows:

$$O = 2P^2 A / QL \quad (15)$$

In the case of a collection means 10 which comprises a single thin lens as illustrated in FIG. 4, the values of P and Q are related by the focal length of the lens as set forth in equation (1). If P is made equal to Q, the system will be symmetrical and $$P = Q = 2f \quad (16)$$

Figure 1:
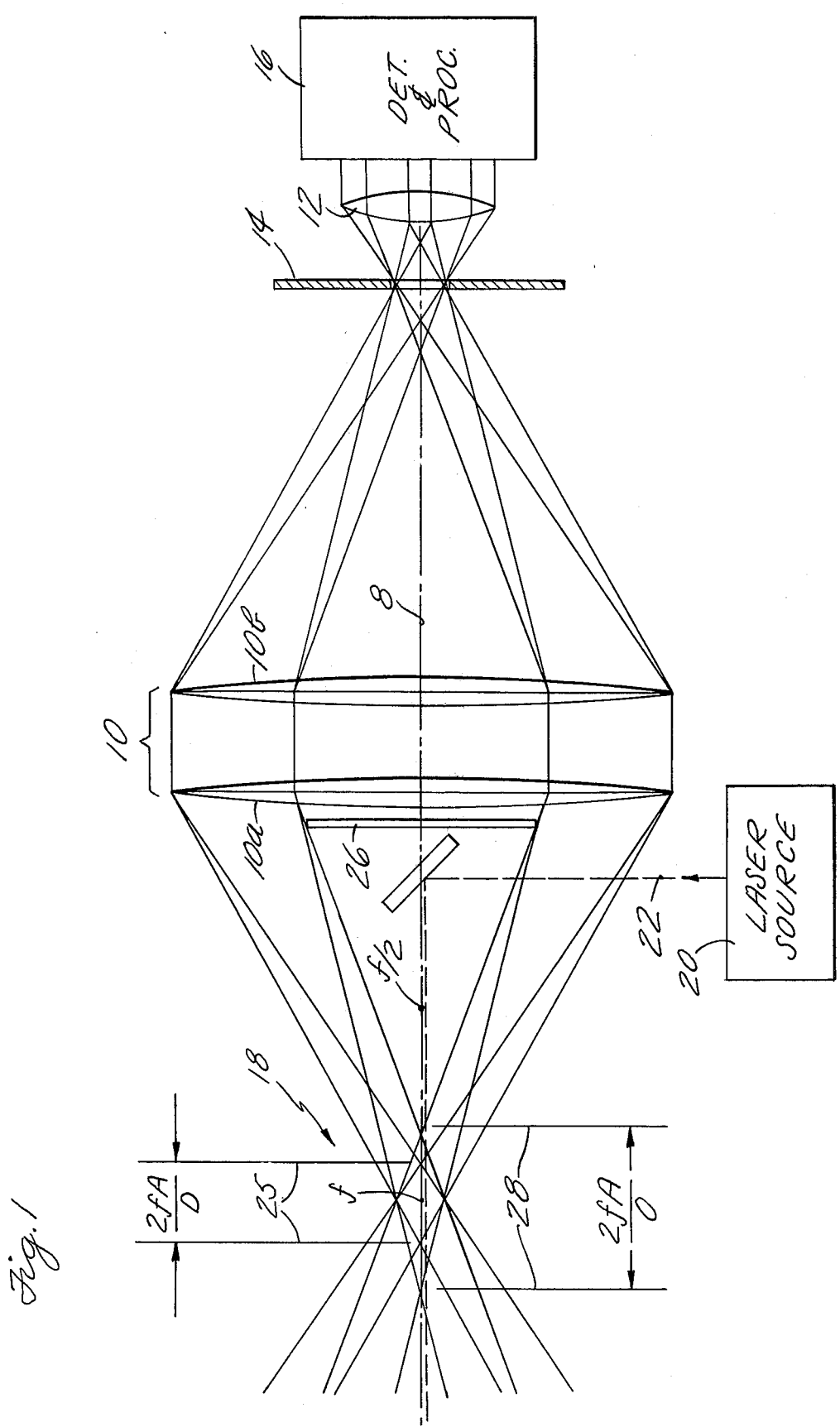
FIG. 1 is an exemplary illustration of a first embodiment of the present invention, employing a collection lens with an obscuration disc on the specimen side thereof.

Referring now to FIG. 1, a coaxial optical system having an optical axis 8 comprises a first embodiment of the present invention. The collection means 10 comprises a doublet including a pair of similar thin lenses 10a, 10b coaxially disposed with respect to the optical axis 8; these lenses may have the same focal length, as generally depicted in FIG. 1; or their focal lengths may differ, as generally depicted in FIG. 4. In either case, light emanating from the focal point (f) of the lens 10a at the axis will be collimated between the lenses and will converge at the focal point of the lens 10b, as shown in FIG. 1, and as is well known in the art. The use of two lenses simply reduces aberration effects and permits easy adjustment of the focal point f, as is known in the art; a single lens may be used if desired.

The collimating lens 12 is also coaxially disposed with respect to the optical axis; the aperture 14 is coaxially disposed with respect to the optical axis 8 at the focal point of the lens 10b and between it and the collimating lens 12. The collimating lens 12 provides collected light to detection and processing means 16 which may be any type well known in the art, as exemplified in the aforementioned text of Lapp and Penney. For Stokes and anti-Stokes temperature measuring, the detection and processing means 16 may comprise a photodetector with suitable beam steering mirrors, wavelength filters, and the like, to permit determining the ratio of Stokes and anti-Stokes light scattering in a specimen. Further specific details of this embodiment are set forth in: Eckbreth, Alan C., "Laser Raman Gas Thermometry", AIAA Paper No. 74-1144, AIAA/SAE 10th Propulsion Conference, San Diego CA, Oct. 21-23, 1974. For other phenomena diagonstics, other known apparatus may be used. The specimen may be located in a sample volume within the region generally designated as 18, including the optical axis 8 and the image of the aperture 14 (at f in FIG. 1). The radiation of the specimen may be provided by a line source of illumination, such as a laser source 20 having a rather finely collimated energy beam 22 directed toward a turning mirror 24 (see FIG. 3), which may be disposed on the optical axis 8 at an angle to divert the laser energy along the optical axis so as to illuminate the specimen at 18.

The scattering of light from the specimen 18, such as Raman scattering, through the optical system to the detector and processor, as described for FIG. 1 thus far, is exemplary of the prior art as described hereinbefore. In such a system, the collection of scattered light by the light collecting means 10 for application to the detection and processing means 16 takes place from a point f/2 all the way out to infinity. However, for an ideal optical system with a theoretical line of illumination, the aperture 14 affects the light collection in such a way that fifty percent of the light is collected along the axis for a finite distance 25 centered about the focal point f, the distance being equal to twice the focal length ($f$) times the ratio of the diameter (A) of the aperture 14 over the diameter (D) of the lenses in the collection means 10. As described hereinbefore, however, when the particular phenomenon being sensed has a large gradient, such as a very high temperature that exists outside of the finite length 25, it may so swamp the processor that the effects within the finite length are unknown. Thus, there is poor spatial resolution along the optical axis of a coaxial configuration of the type described thus far with respect to FIG. 1.

The improvement of the present invention consists of the obscuration means such as the disc 26 disposed between the specimen and the collection means 10, which severely limits the extent of light collection along the optical axis. In this case $P=Q=f$, so the length of the sample volume is equal to twice the focal length (f) of the lens 10a times the ratio of the diameter (A) of the aperture 14 to the diameter (O) of the obscuration disc 26. Since all of the light is collected in this finite length 28, the fraction of scattered light collected within the finite length 25 is a much greater portion of the total than it would be in the case of the prior art where total light collection is from f/2 to infinity. Specifically, the fraction collected within the finite length 25 is determined, from known classical optics, to be $\frac{1}{2}(1+O/D)$, which is also expressable as $(D+O)/2D$.

As an example, consider an obscuration disc which is half the diameter of the collection means 10. Seventy-five percent of the scattered light is contributed by the area along the shorter length 25, at a cost of only a twenty-five percent decrease in the total collection area. For a fifty percent decrease in the collection area, the ratio of the diameters of the obscuration disc and the collection means 10 would be 1 $\sqrt{2}$; but this would concentrate eighty-five percent of the collected backscattering from the shorter length 25. The decrease in collection efficiency may be compensated for by reducing the f-number of the system, when possible, to increase the total angle subtended by the optical system.

Figure 2:
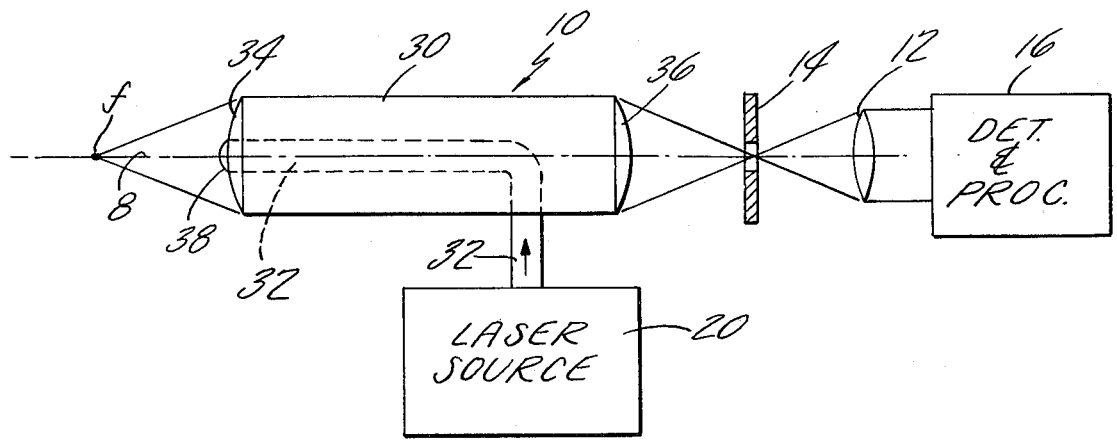
FIG. 2 is an exemplary illustration of a second embodiment of the invention utilizing coaxial light pipes.

A second embodiment of the invention, as illustrated in FIG. 2, employs a self-obscuring collection means 10 consisting of coaxial fiber optic light pipes 30, 32, the energy from a laser source 20 being conducted through the inner, solid light pipe 32, which automatically provides obscuration to the optical system since only the outer, annular light pipe 30 will collect any scattering. The light pipes 30, 32 may be configured for lens action on their ends 34, 36 and 38, respectively, or separate lenses may be provided, all as is well within the skill of the art. This embodiment combines automatic obscuration (to reduce the extent of collection of scattering, thereby to increase the portion of scattering collected in the finite distance about the focal point f) with the obvious advantages of light pipes in directing the source irradiation and the scattered light collection about various routes to implement any practical requirements of a diagnostic system or the like. In FIG. 2, the light pipes 30, 32 may most advantageously consist of bundles of optical fibers of very small diameter, although this is not illustrated in detail in FIG. 2 for simplicity.

Figure 3:
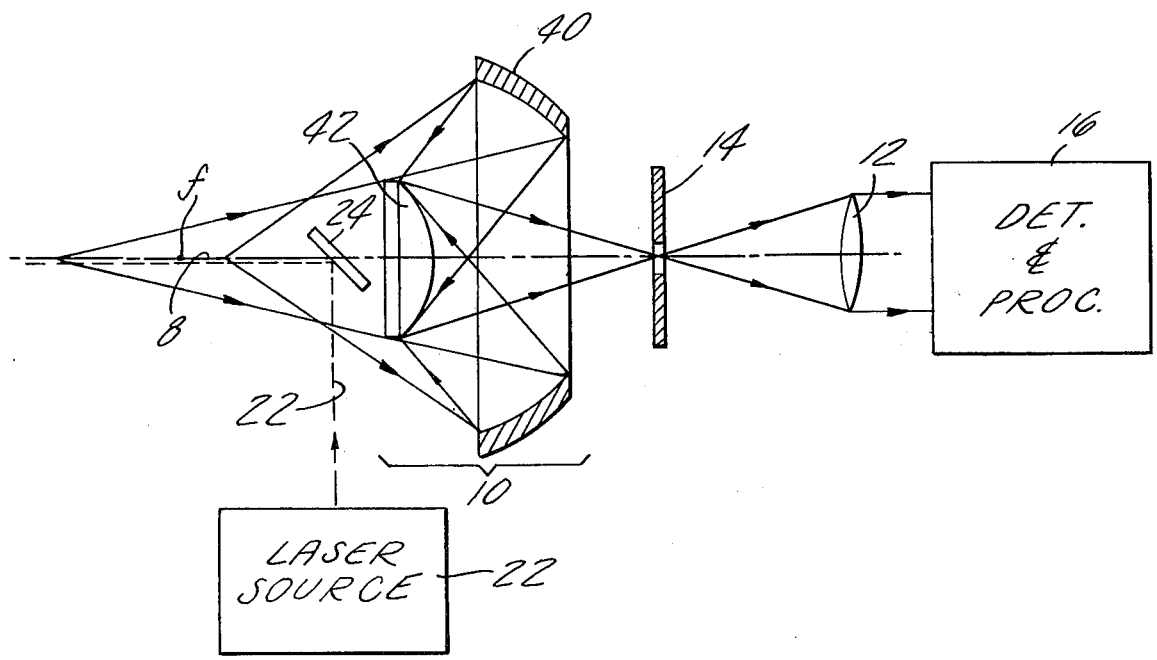
FIG. 3 is an exemplary illustration of a third embodiment of the present invention utilizing Cassegrainian reflective optics.

Referring now to FIG. 3, a third embodiment of the present invention employs, as a self-obscuring collection means 10, Cassegrainian type reflective optics, including an annular primary reflector 40 and a convex secondary reflector 42, of the type known in the art. Scattering collected by the primary 40 is reflected to the secondary 42 which in turn reflects through the aperture 14 in a well known way. In a classical Cassegrainian system, the ideal situation is to reduce the obscuration caused by the secondary 42 to as small an amount as possible; this is normally achieved by the curvilinear shaping of the primary and the secondary 40, 42. However, in this case, a large amount of obscuration can be endured. The configuration of the Cassegrainian system may deviate widely from the normal, most efficient configuration, and may in fact employ a substantially flat reflective surface as a secondary, or may take the form of an axicon type of reflective system in which both the primary and the secondary have conical surfaces. Consider, first, that for complete light collection along the entire length of the optical axis 8, the primary reflector 40 would need to be a complete dish (rather than annular, as in a Cassegrainian system). Any amount of secondary which obscures a portion of it reduces the total extent of the collection area. But in this case, the ratio of the actual collection area to the total potential area of a given diameter of collection reflector 40 will be quite small in accordance with the teachings of the present invention. That is, the area of responsiveness of the reflector 40 in the present invention, as obscured by the secondary reflector 42, might be only twenty-five percent of the total potential for a dish. However, this concomitantly limits the extent of the collecting area along the axis due to the obscuration provided by an excessively large secondary 42 in the same fashion as described with respect to the refractive system of FIG. 1. One advantage of the Cassegrainian system as illustrated in FIG. 3 (as well as the other embodiments) is that the turning mirror 24, lying in front of the obscuration provided by the secondary 42, does not interfere with the operation of this system at all.

All the embodiments herein refer to a laser source and to optical systems. As used herein, the particular frequency of the electromagnetic radiation, utilized for illumination of the specimen in order to provide scattering of interest, is not important. Thus, lasers of any available frequency may be used to suit a particular utilization of the invention; similarly, collimated light which is not necessarily coherent may be used in some instances. Thus, the term optics is not to be limited herein to relationships with respect to the visible spectrum of radiation. Similarly, some of the details of the systems disclosed in the various embodiments are irrelevant to the practice of the present invention, which relates to limitation of the extent of light collection of an optical system by means of an obscuration disc in conjunction with the concentration of collection in a limited area by virtue of an aperture, thereby to enhance the spatial resolution of the device by increasing the proportion of scattering collected from a finite length (the resolution distance) of the device. Similarly, although described with respect to light scattering diagnostics (primarily Raman scattering), it is obvious that the system may be employed for other purposes as well. Thus, although the invention has been shown and described with respect to preferred embodiments thereof, it should be understood by those skilled in the art that the foregoing and various other changes and omissions in the form and detail thereof may be made therein and thereto without departing from the spirit and the scope of the invention.

Having described typical embodiments of our invention, that which we claim as new and desire to secure by Letters Patent is:

1. Coaxial optical apparatus having increased spatial resolution along a desired length L, comprising:
    an aperture of diameter A and having an optical axis;
    collection means, having a focal length f, disposed on said optical axis on a first side of said aperture and spaced a distance Q therefrom, said collection means collecting light from a sample volume including the image of said aperture spaced along said optical axis a distance $P+Q$ from said aperture and on the opposite side of said collection means therefrom, where $1/f = 1/P + 1/Q$;
    illumination means including a source of radiation for illuminating the sample volume from a point on said optical axis between the sample volume and said collection means in a manner such that backscattering of radiation from the sample volume as result thereof is collected by said collection means;
    optically responsive means disposed along said optical axis on a second side of said aperture for detecting and processing backscattered radiation directed from said volume through said aperture by said collection means and
    obscuration means consisting of a disk having an effective obscuring diameter equal to $2\ P^2A/QL$ disposed on said optical axis between said aperture and the sample volume for limiting the extent of the sample volume along said optical axis to said desired length L.

2. Apparatus according to claim 1 wherein said collection means comprises refractive lens means, said obscuration means comprises an opaque disc, and said illumination means comprises a radiation-turning mirror disposed along said axis between the sample volume and said disc.

3. Apparatus according to claim 2 wherein said collection means comprises a doublet of two lenses of substantially equal focal length f, such that $f = P = Q$, and the effective obscuring diameter of said obscuration means is equal to $2fA/L$.

4. Apparatus according to claim 1 wherein said collection means comprises an annular fiber optic light pipe and wherein said illuminating means comprises a second fiber optic light pipe disposed coaxially within at least part of said annular fiber optic light pipe, said second fiber optic light pipe also comprising said obscuration means.

5. Apparatus according to claim 1 wherein said collection means and said obscuration means comprise a reflective, Cassegrainian type of apparatus having a primary reflector and a secondary reflector, the obscuration means comprising a first surface of said secondary reflector, said illumination means including a radiation-turning mirror disposed adjacent to said first surface of said secondary reflector.

* * * * *